United States Patent
Bouchy

(10) Patent No.: US 12,403,459 B2
(45) Date of Patent: *Sep. 2, 2025

(54) CATALYST BASED ON IZM-2 ZEOLITE WITH A LOW CONTENT OF ALKALI METAL, AND USE THEREOF FOR THE ISOMERIZATION OF AROMATIC C8 CUTS

(71) Applicant: IFP Energies Nouvelles, Rueil-Malmaison (FR)

(72) Inventor: Christophe Bouchy, Rueil-Malmaison (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 235 days.

This patent is subject to a terminal disclaimer.

(21) Appl. No.: 17/783,734

(22) PCT Filed: Dec. 9, 2020

(86) PCT No.: PCT/EP2020/085218
§ 371 (c)(1),
(2) Date: Jun. 9, 2022

(87) PCT Pub. No.: WO2021/122199
PCT Pub. Date: Jun. 24, 2021

(65) Prior Publication Data
US 2023/0008326 A1    Jan. 12, 2023

(30) Foreign Application Priority Data
Dec. 17, 2019   (FR) ...................................... 1914592

(51) Int. Cl.
*B01J 29/14*       (2006.01)
*B01J 21/04*       (2006.01)
*B01J 29/74*       (2006.01)
*C07C 5/27*        (2006.01)

(52) U.S. Cl.
CPC .............. *B01J 29/74* (2013.01); *B01J 21/04* (2013.01); *C07C 5/2775* (2013.01); *B01J 2229/42* (2013.01); *C07C 2521/04* (2013.01); *C07C 2529/74* (2013.01)

(58) Field of Classification Search
CPC . C01B 39/48; Y02P 20/52; B01J 21/04; B01J 29/74; B01J 29/76; B01J 2229/20; B01J 2229/42; B01J 2229/186; B01J 35/394; B01J 35/615; B01J 35/635; B01J 35/647; B01J 35/69; B01J 37/0209; B01J 37/0213; C07C 5/2775; C07C 5/2708; C07C 2521/04; C07C 2529/74; C07C 2529/76; C07C 15/08
USPC ...................... 502/60, 63, 64, 66, 68, 69, 74
See application file for complete search history.

(56) References Cited

U.S. PATENT DOCUMENTS

| | | | |
|---|---|---|---|
| 4,467,129 A | 8/1984 | Iwayama et al. | |
| 4,482,773 A | 11/1984 | Chu et al. | |
| 5,055,443 A | 10/1991 | Mercier et al. | |
| 6,057,486 A | 5/2000 | Merlen et al. | |
| 7,091,190 B2 | 8/2006 | Marcelletti et al. | |
| 8,247,630 B2 | 8/2012 | Bogdan et al. | |
| 8,361,435 B2 | 1/2013 | Fecant et al. | |
| 8,629,073 B2 | 1/2014 | Guillon et al. | |
| 9,597,670 B2 | 3/2017 | Ballegoy et al. | |
| 10,183,902 B2 | 1/2019 | Bouchy | |
| 2009/0093662 A1 | 4/2009 | Whitchurch et al. | |
| 2011/0180455 A1* | 7/2011 | Bouchy ................... | C10G 47/20 208/49 |
| 2014/0135550 A1* | 5/2014 | Guillon .................... | B01J 23/42 585/481 |
| 2014/0296601 A1 | 10/2014 | Rane et al. | |

OTHER PUBLICATIONS

Machine Translation of FR 2 934 794, Feb. 12, 2010, 39 pages.*
Yunxiang Li et al: "Supplementary Information of "Microporous pure-silica IZM-2"", Microporous and Mesoporous Materials, Sep. 21, 2016 (Sep. 21, 2016), pp. 1-11, XP055723402.
Filipe Marques Mota et al: "IZM-2: A promising new zeolite for the selective hydroisomerization of long-chain n-alkanes", Journal of Catalysis., vol. 301, Feb. 28, 2013 (Feb. 28, 2013), US, pp. 20-29, XP055495311, ISSN: 0021-9517, DOI: 10.1016/j.jcat.2013.01.017.
Li Yunxiang et al: "Microporous pure-silica IZM-2", Microporous and Mesoporous Materials, Elsevier, Amsterdam, NL, vol. 237, Sep. 21, 2016 (Sep. 21, 2016), pp. 222-227, XP029777580, ISSN 1387-1811, DOI: 10.1016/J.MICROMESO.2016.09.033.
International Search Report PCT/EP2020/085218 dated Mar. 2, 2021 (pp. 1-3).

* cited by examiner

*Primary Examiner* — Smita S Patel
(74) *Attorney, Agent, or Firm* — Csaba Henter; MILLEN, WHITE, ZELANO & BRANIGAN, P.C.

(57) ABSTRACT

A catalyst containing a IZM-2 zeolite and a specific content of alkali metal or alkaline-earth metal compounds, and a process for the isomerization of an aromatic C8 cut using the catalyst.

9 Claims, No Drawings

CATALYST BASED ON IZM-2 ZEOLITE WITH A LOW CONTENT OF ALKALI METAL, AND USE THEREOF FOR THE ISOMERIZATION OF AROMATIC C8 CUTS

TECHNICAL FIELD

Sources of aromatics containing eight carbon atoms are mainly obtained from the reforming process (reformate) and the steam cracking process (pyrolysis gasolines). The distribution of aromatics containing eight carbon atoms in these cuts is variable: generally from 10% to 30% of ethylbenzene, the remainder being formed from the three xylene isomers: para-xylene, meta-xylene and ortho-xylene. Typically, the distribution within this remainder of xylenes is 50% meta-xylene, 25% ortho-xylene and 25% para-xylene. Within this xylene remainder, para-xylene is a highly sought isomer. Specifically, via dimethyl terephthalate and terephthalic acid, said isomer allows the production of polyester fibres used for clothing and resins and films made of polyethylene terephthalate (PET). It is thus desirable to maximize the production of para-xylene at the expense of the other aromatics containing eight carbon atoms. This is performed by implementing catalytic isomerization processes. After extraction of the para-xylene, the residual cut, rich in meta-xylene, ortho-xylene and ethylbenzene, is sent to a catalytic isomerization unit which restores a mixture of aromatics containing eight carbon atoms in which the proportion of the xylenes is close to the thermodynamic equilibrium and the amount of ethylbenzene is reduced by means of conversion of the ethylbenzene. This mixture is again sent into a para-xylene extraction unit and the residual cut is sent to the isomerization unit. An "aromatic C8 loop" is thus created, which maximizes the production of para-xylene (E. Guillon, P. Leflaive, Techniques de l'Ingénieur, J5920, V3). An isomerization unit may be used to isomerize the xylenes to para-xylene and to convert the ethylbenzene into benzene via the ethylbenzene dealkylation reaction. In this case, the cut is said to have undergone "dealkylating" isomerization. The residual cut may also be sent to a catalytic isomerization unit, to isomerize the xylenes to para-xylene and to convert the ethylbenzene into xylenes via the ethylbenzene dealkylation reaction. The cut is then said to have undergone "isomerizing" isomerization. These industrial processes generally use heterogeneous catalysts used in a fixed bed and working in the vapour phase under hydrogen pressure. These two types of processes differ by the operating conditions and by the formulation of the catalysts used (by their nature and/or their content of hydro-dehydrogenating and/or acid functions). The present invention falls within the field of "isomerizing" isomerization.

In the case of "isomerizing" isomerization, the catalyst is of difunctional type and contains both an acidic function (generally borne by at least one zeolite) and a hydro-dehydrogenating function borne by a noble metal (generally platinum). Specifically, it has been demonstrated that the isomerization of ethylbenzene to xylenes involves a mechanism of difunctional type. Ethylbenzene is first hydrogenated to ethylcyclohexenes on the metallic sites, and these cycloolefin intermediates are then isomerized to dimethylcyclohexenes on the Brønsted acid sites. Finally, the dimethylcyclohexenes are dehydrogenated to xylenes on the metallic sites. The use of a strong hydro-dehydrogenating function such as platinum also induces the production of naphthenic rings by hydrogenation of the corresponding aromatic rings.

In addition to the desired isomerization reactions, it is desirable to limit the side reactions such as:
 dealkylation of ethylbenzene to benzene and ethylene;
 dismutation of ethylbenzene to diethylbenzene and benzene, or of xylenes to toluene and aromatics containing 9 carbon atoms;
 alkyl transfer between ethylbenzene and the xylenes; and between the xylenes themselves;
 opening of the naphthenic rings and cracking.

All these reactions give rise to the production of less valuable molecules, which are not recycled into the "aromatic C8 loop" and are considered as net losses to the process. All the molecules other than the cyclic molecules containing eight carbon atoms are thus considered as net losses.

The isomerization reactions and the side reactions are mainly catalysed by the acid function. The properties of zeolite (number and strength of the Brønsted acid sites, topology of the microporous network, etc.), acting as an acid function, thus have a direct impact on the properties of the difunctional catalyst, and notably on its selectivity.

The catalysis of the isomerization of an aromatic C8 cut into xylenes has thus been the subject of numerous patents relating to various zeolites. Among the zeolites used in the isomerization of an aromatic C8 cut is ZSM-5, used alone or as a mixture with other zeolites, for instance mordenite. These catalysts are notably described in patents U.S. Pat. Nos. 4,467,129 B and 4,482,773 B. Other catalysts mainly based on mordenite have been described, for example, in patent FR 2 477 903 B. Catalysts that have also been proposed include catalysts based on a zeolite of EUO structure type (EP 923 987) or based on a zeolite of MTW structure type (WO 2005 065380 A, WO 2010 000652 A, US 2014 0296601 A) or based on a UZM-8 zeolite in patent U.S. Pat. No. 7,091,190 B.

These examples illustrate the continuous research performed to develop ever more effective catalysts for the isomerization of aromatic C8 cuts, notably while minimizing the production of net losses via the use of appropriate zeolites. For a catalyst involving a given zeolite, it is reported that the presence of alkali metal and/or alkaline-earth metal in the catalyst makes it possible to improve the selectivity towards isomerization of said catalyst, but generally at the expense of a loss of activity of said catalyst. The studies by Moreau et al. (Microporous and Mesoporous Materials 51 (2002) 211-221; Applied Catalysis A: General 230 (2002) 253-262) related to the study of catalysts containing mordenite zeolites partially exchanged with sodium. It is shown that exchange with sodium improves the selectivity towards isomerization during the transformation of m-xylene and during the transformation of ethylbenzene. In both cases, this gain in selectivity is accompanied by a loss of activity of the catalyst caused by the partial neutralization of the acid sites with the sodium. The studies by L. D. Fernandes et al. (Journal of Catalysis 177 (1998) 363-337) related, inter alia, to the study of catalysts containing mordenite zeolites not exchanged or exchanged with calcium. The presence of calcium makes it possible to improve the selectivity of the catalysts during the transformation of ethylbenzene. A loss of activity is also reported in the presence of calcium.

Patent EP 0 458 378 B1 claims a catalyst for the isomerization of aromatic C8 compounds, containing a metal from group VIII, a binder and a zeolite containing 2% to 3% of an alkali metal. The examples involve catalysts using mordenite zeolites with a variable sodium content. The examples show that the presence of sodium in the MOR zeolite at between 2% and 3% by weight makes it possible to reduce the losses of C8 aromatics.

Patent application US 2009/0 093 662 A1 describes a catalyst for the isomerization of C8 aromatics, containing a zeolite of MTW type, a binder, a noble metal and at least one alkali metal which may be lithium, sodium, potassium, rubidium, caesium, francium or a combination of these elements, in which the total amount of alkali metal in the catalyst is at least about 100 ppm by weight relative to the mass of the catalyst. Preferably, the catalyst does not comprise any alkali metals other than those already included in the zeolite and/or the binder. Preferably, the total content of alkali metals in the catalyst is at least about 200 ppm and preferably 300 ppm and preferably less than about 2500 ppm and preferably 2000 ppm and preferably less than 1000 ppm by weight. Preferably, no washing with ammonium nitrate solution is performed, so as to enable the alkali metals that are present to remain on the catalyst. However, if the catalyst and in particular the zeolite and/or the binder have an excessively high alkali metal content, washing with ammonium nitrate or ammonium hydroxide solution may be performed so that the catalyst has the desired alkali metal content. The examples involve catalysts using an MTW zeolite and binders and also variable contents of sodium and potassium. In particular, the examples show that the catalysts with a total content of alkali metals of greater than about 200 ppm have a loss of cyclic molecules containing eight carbon atoms (C8RL) of between 2.0 mol % and 2.4 mol %, whereas catalysts comprising a different alumina binder comprising a smaller content of alkali metals than the catalysts according to the invention have a higher loss of cyclic molecules containing eight carbon atoms (C8RL) of between 2.6 mol % and 3.4 mol %.

In its studies, the Applicant has recently developed a new zeolite, IZM-2 zeolite (FR 2 918 050 A1, incorporated into the present patent application by reference), and also its use in a catalyst for the isomerization of a cut containing at least one aromatic compound containing eight carbon atoms (FR 2 934 793 A1 and FR 3 054 454 A1).

During its studies directed towards developing a catalyst for the isomerization of aromatic C8 cuts, comprising said IZM-2 zeolite, the Applicant has discovered a surprising effect of the presence of alkali metal and/or alkaline-earth metal on the performance qualities of the catalyst. Surprisingly, the Applicant has demonstrated that a catalyst containing a total content of alkali metal and/or alkaline-earth metal that is reduced relative to the catalysts of the prior art has increased activity without reducing its selectivity towards isomerization relative to the catalysts of the prior art.

Thus, one object of the present invention is to provide a novel catalyst for the isomerization of aromatic C8 cuts, based on IZM-2 zeolite, said catalyst containing a limited amount of alkali metal and/or alkaline-earth metal, to limit the production of net losses.

Another subject of the present invention relates to a process for the isomerization of a cut containing at least one aromatic compound containing eight carbon atoms per molecule, said process comprising placing said aromatic cut in contact with at least said catalyst according to the invention present in a catalytic reactor.

SUMMARY OF THE INVENTION

In particular, the present invention relates to a catalyst comprising at least one IZM-2 zeolite, at least one matrix and at least one metal from group VIII of the Periodic Table of the Elements, said catalyst being characterized in that the total weight ratio of alkali metal and/or alkaline-earth metal elements in said catalyst is less than 200 ppm by weight relative to the total mass of said catalyst, preferably less than 150 ppm, preferably less than 100 ppm, preferably less than 90 ppm by weight, preferably less than 85 ppm by weight, more preferably less than 80 ppm by weight, very preferably less than 75 ppm by weight and even more preferably less than 70 ppm by weight and greater than 20 ppm by weight and preferably greater than 30 ppm by weight.

In the continuation of the present document, the weight contents provided are considered relative to the dry mass of solid. The dry mass of solid corresponds to the mass of the solid after calcining in air for 2 hours at 1000° C. in a muffle furnace.

For the purposes of the present invention, the various embodiments presented may be used alone or in combination with each other, without any limit to the combinations when this is technically feasible.

For the purposes of the present invention, the various ranges of parameters for a given step, such as the pressure ranges and the temperature ranges, may be used alone or in combination. For example, for the purposes of the present invention, a preferred range of pressure values can be combined with a more preferred range of temperature values.

The catalyst according to the invention is advantageously used in a process for the isomerization of an aromatic cut comprising at least one aromatic compound containing eight carbon atoms per molecule, under the following operating conditions:
 a temperature of from 300° C. to 500° C.,
 a partial pressure of hydrogen of from 0.3 to 1.5 MPa,
 a total pressure of from 0.45 to 1.9 MPa, and
 a feed space velocity, expressed in kilograms of feedstock introduced per kilogram of catalyst and per hour, of from 0.25 to 30 h$^{-1}$.

It has been discovered, surprisingly, that the catalyst according to the invention comprising at least one IZM-2 zeolite, a matrix, at least one metal from group VIII of the Periodic Table of the Elements, and a total weight content of alkali metal and/or alkaline-earth metal elements in said catalyst of less than 200 ppm by weight and greater than 20 ppm has improved catalytic performance qualities in terms of activity, without loss of selectivity, during a process for the isomerization of an aromatic feedstock comprising at least one aromatic cut comprising at least one aromatic compound containing eight carbon atoms per molecule.

Such a catalyst is substantially more active than a catalyst comprising an IZM-2 zeolite in which the alkali metal and/or alkaline-earth metal content is greater than 200 ppm. Reducing the alkali metal content to contents of less than 200 ppm thus makes it possible to improve the activity of such a catalyst without loss of selectivity. This may be exploited in two ways by a person skilled in the art: increasing the activity of the catalyst for the same content of IZM-2 or maintaining the activity of the catalyst by reducing the content of IZM-2 zeolite in the catalyst.

The total weight content of alkali metal and/or alkaline-earth metal elements in said catalyst is measured by atomic absorption spectroscopy on a Varian Spectr'AA 240FS Flame Atomic Absorption Spectrometer (FAAS) after dissolving the solid by wet mineralization of the solid. The term "mineralization of the solid" means the dissolution of said solid, which is typically performed in concentrated aqueous solutions of perchloric, hydrofluoric and hydrochloric acids. It may be performed at elevated temperature on a hotplate or by microwave.

DESCRIPTION OF THE EMBODIMENTS

The present invention relates to a catalyst comprising, and preferably consisting of, at least one IZM-2 zeolite preferably containing silicon atoms and optionally aluminium atoms, at least one matrix and at least one metal from group VIII of the Periodic Table of the Elements, said catalyst being characterized in that the total weight content of alkali metal and/or alkaline-earth metal elements in said catalyst is less than 200 ppm by weight and greater than 20 ppm by weight relative to the total mass of said catalyst.

Preferably, said catalyst has a total weight content of alkali metal and/or alkaline-earth metal elements of less than 150 ppm by weight relative to the total mass of said catalyst, preferably less than 100 ppm by weight, preferably less than 90 ppm by weight, preferably less than 85 ppm by weight, preferably less than 80 ppm by weight, more preferably less than 75 ppm by weight and even more preferably less than 70 ppm by weight and greater than 20 ppm by weight and preferably greater than 30 ppm by weight.

Preferably, said catalyst does not comprise any added alkali metal and/or alkaline-earth metal elements, other than those associated with the zeolite and/or with the matrix used in said catalyst.

Said catalyst according to the invention more particularly comprises, and preferably consists of:
  from 1% to 90% by weight, preferably from 3% to 80% by weight and even more preferably from 4% to 60% by weight of IZM-2 zeolite relative to the total mass of said catalyst according to the invention,
  from 0.01% to 4% and preferably from 0.05% to 2% by weight of at least one metal from group VIII of the Periodic Table of the Elements, preferably platinum, relative to the total mass of said catalyst,
  optionally from 0.01% to 2% by weight and preferably from 0.05% to 1% by weight of at least one additional metal chosen from the group formed by the metals from groups IIIA, IVA and VIIB, relative to the total mass of said catalyst,
  optionally a sulfur content, preferably such that the ratio of the number of moles of sulfur to the number of moles of the metal(s) of group VIII is between 0.3 and 3,
  a total weight content of alkali metal and/or alkaline-earth metal elements of less than 200 ppm by weight relative to the total mass of said catalyst, preferably less than 150 ppm, preferably less than 100 ppm, preferably less than 90 ppm by weight, preferably less than 85 ppm by weight, preferably less than 80 ppm by weight, very preferably less than 75 ppm by weight and even more preferably less than 70 ppm by weight and greater than 20 ppm by weight and preferably greater than 30 ppm by weight.
  at least one matrix, preferably alumina, providing the remainder to 100% in the catalyst.

IZM-2 Zeolite

In accordance with the invention, the catalyst comprises an IZM-2 zeolite. IZM-2 zeolite has an X-ray diffraction diagram which includes at least the lines recorded in Table 1. IZM-2 zeolite has a crystalline structure.

Advantageously, the diffraction diagram is obtained by radiocrystallographic analysis by means of a diffractometer using the conventional powder method with the $K_{\alpha 1}$ radiation of copper ($\lambda$=1.5406 Å). On the basis of the position of the diffraction peaks represented by the angle 2θ, the lattice constant distances $d_{hkl}$ characteristic of the sample are calculated using the Bragg relationship. The measurement error $\Delta(d_{hkl})$ on $d_{hkl}$ is calculated by means of the Bragg relationship as a function of the absolute error $\Delta(2\theta)$ assigned to the measurement of 2θ. An absolute error $\Delta(2\theta)$ equal to ±0.02° is commonly accepted. The relative intensity Ire' assigned to each value of $d_{hkl}$ is measured according to the height of the corresponding diffraction peak. The X-ray diffraction diagram of the IZM-2 zeolite contained in the catalyst according to the invention includes at least the lines at the values of $d_{hkl}$ given in Table 1. In the column of the $d_{hkl}$ values, the mean values of the interplanar spacings are given in Angstroms (Å). Each of these values must be assigned the measurement error $\Delta(d_{hkl})$ of between ±0.6 Å and ±0.01 Å.

| 2 theta (°) | $d_{hkl}$ (Å) | Irel | 2 theta (°) | $d_{hkl}$ (Å) | Irel |
|---|---|---|---|---|---|
| 5.07 | 17.43 | vw | 19.01 | 4.66 | vw |
| 7.36 | 12.01 | VS | 19.52 | 4.54 | vw |
| 7.67 | 11.52 | VS | 21.29 | 4.17 | m |
| 8.78 | 10.07 | S | 22.44 | 3.96 | w |
| 10.02 | 8.82 | vw | 23.10 | 3.85 | mw |
| 12.13 | 7.29 | vw | 23.57 | 3.77 | w |
| 14.76 | 6.00 | vw | 24.65 | 3.61 | vw |
| 15.31 | 5.78 | vw | 26.78 | 3.33 | w |
| 15.62 | 5.67 | vw | 29.33 | 3.04 | vw |
| 16.03 | 5.52 | vw | 33.06 | 2.71 | vw |
| 17.60 | 5.03 | vw | 36.82 | 2.44 | vw |
| 18.22 | 4.87 | vw | 44.54 | 2.03 | vw | where VS = very strong; S = strong; m = medium; mw = moderately weak; w = weak; vw = very weak.

The relative intensity $I_{rel}$ is given as a relative intensity scale in which a value of 100 is attributed to the most intense line in the X-ray diffraction diagram: vw<15; 15≤w<30; 30≤mw<50; 50≤m<65; 65≤S<85; VS≥85.

Said solid IZM-2 advantageously has a chemical composition expressed on an anhydrous basis, in terms of moles of oxides, defined by the following general formula: XO2: aY2O3:bM2/nO, in which X represents at least one tetravalent element, Y represents at least one trivalent element and M is at least one alkali metal and/or alkaline-earth metal of the valency n. In said formula given above, a represents the number of moles of Y2O3 and a is between 0 and 0.5, very preferentially between 0 and 0.05 and even more preferably between 0.0016 and 0.02 and b represents the number of moles of M2/nO and is between 0 and 1, preferably between 0 and 0.5 and even more preferably between 0.005 and 0.5.

Preferably, X is chosen from silicon, germanium, titanium and a mixture of at least two of these tetravalent elements; very preferentially, X is silicon; and Y is preferentially chosen from aluminium, boron, iron, indium and gallium; very preferentially, Y is aluminium. M is preferentially chosen from lithium, sodium, potassium, calcium, magnesium and a mixture of at least two of these metals, and very preferentially M is sodium. Preferably, X represents silicon, said crystalline solid IZM-2 is then an entirely silicic solid when the element Y is absent from the composition of said solid IZM-2. It is also advantageous to use as element X a mixture of several elements X, in particular a mixture of silicon with another element X chosen from germanium and titanium, preferably germanium. Thus, when silicon is present as a mixture with another element X, the crystalline solid IZM-2 is then a crystalline metallosilicate having an X-ray diffraction diagram identical to that described in Table 1 when it is in its calcined form. Even more preferably and in the presence of an element Y, X being silicon and Y being aluminium: said crystalline solid IZM-2 is then a crystalline aluminosilicate having an X-ray diffraction diagram identical to that described in Table 1 when it is in its calcined form.

More generally, said solid IZM-2 used in the support of the catalyst implemented in the process according to the invention advantageously has a chemical composition expressed by the following general formula: $XO_2:aY_2O_3:bM_{2/n}O:cR:dH_2O$ in which R represents an organic species including two quaternary nitrogen atoms, X represents at least one tetravalent element, Y represents at least one trivalent element and M is an alkali metal and/or alkaline-earth metal of valency n; a, b, c and d representing, respectively, the number of moles of $Y_2O_3$, $M_{2/n}O$, R and $H_2O$ and a is between 0 and 0.5, b is between 0 and 1, c is between 0 and 2 and d is between 0 and 2. This formula and the values taken by a, b, c and d are those for which said solid IZM-2 is preferentially in its calcined form.

More precisely, said solid IZM-2, in its raw synthetic form, advantageously has a chemical composition expressed by the following general formula: $XO_2:aY_2O_3:bM_{2/n}O:cR:dH_2O$ (I) in which R represents an organic species including two quaternary nitrogen atoms, X represents at least one tetravalent element, Y represents at least one trivalent element and M is an alkali metal and/or alkaline-earth metal of valency n; a, b, c and d representing, respectively, the number of moles of $Y_2O_3$, $M_{2/n}O$, R and $H_2O$ and a is between 0 and 0.5, b is between 0 and 1, c is between 0.005 and 2 and preferably between 0.01 and 0.5, and d is between 0.005 and 2 and preferably between 0.01 and 1.

In formula (I) given above to define the chemical composition of said crystalline solid IZM-2 in its raw synthetic form, the value of a is between 0 and 0.5, very preferentially between 0 and 0.05 and even more preferably between 0.0016 and 0.02. Preferably, b is between 0 and 1, very preferably b is between 0 and 0.5 and even more preferably b is between 0.005 and 0.5. The value of c is between 0.005 and 2, advantageously between 0.01 and 0.5. The value taken by d is between 0.005 and 2, preferably between 0.01 and 1.

In its crude synthetic form, i.e. obtained directly from the synthesis and prior to any calcination step well known to those skilled in the art, said solid IZM-2 advantageously includes at least the organic species R containing two quaternary nitrogen atoms such as that described hereinbelow, or the decomposition products thereof or precursors thereof. According to a preferred embodiment of the invention, in formula (I) given above, the element R is 1,6-bis (methylpiperidinium)hexane, the structural formula of which is given below. Said organic species R, which acts as structuring agent, may be removed via the conventional routes known in the prior art, such as thermal and/or chemical treatments.

A process for preparing IZM-2 zeolite is taught in patent FR 2 918 050 B incorporated herein by reference.

Advantageously, in the case where X is silicon and Y is aluminium, an aqueous mixture including at least one source of at least one oxide $SiO_2$, optionally at least one source of at least one oxide $Al_2O_3$, optionally at least one source of at least one alkali metal and/or alkaline-earth metal of valency n, and preferably at least one organic species R including two quaternary nitrogen atoms, is reacted, the mixture preferentially having the following molar composition:

$SiO_2/Al_2O_3$: at least 2, preferably at least 20, more preferably from 60 to 600,
$H_2O/SiO_2$: 1 to 100, preferably from 10 to 70,
$R/SiO_2$: 0.02 to 2, preferably from 0.05 to 0.5,
$M_{2/n}O/SiO_2$: 0 to 1, preferably from 0.005 to 0.5, where M is one or more alkali metals and/or alkaline-earth metals chosen from lithium, sodium, potassium, calcium and magnesium, and a mixture of at least two of these metals; preferably, M is sodium. Advantageously, the element R is 1,6-bis(methylpiperidinium) hexane.

The Si/Al mole ratio of IZM-2 zeolite may also be adjusted to the desired value via methods of post-treatment of the IZM-2 zeolite obtained after synthesis. Such methods are known to those skilled in the art and make it possible to perform dealumination or desilication of the zeolite. Preferably, the Si/Al mole ratio of the IZM-2 zeolite included in the composition of the catalyst according to the invention is adjusted by means of a suitable choice of the conditions for synthesis of said zeolite.

Among the IZM-2 zeolites, it is usually preferred to use IZM-2 zeolites in which the silicon/aluminium (Si/Al) overall atomic ratio is greater than about 3 and more preferably IZM-2 zeolites in which the Si/Al ratio is between 5 and 200 and even more preferably between 10 and 150.

Thus, according to a preferred embodiment of the process for preparing said crystalline solid IZM-2, an aqueous mixture including silicon oxide, optionally alumina, 1,6-bis (methylpiperidinium)hexane dibromide and sodium hydroxide is reacted. According to another preferred embodiment of the process according to the invention, an aqueous mixture including silicon oxide, optionally alumina and 1,6-bis(methylpiperidinium)hexane dihydroxide is reacted.

The process for preparing said crystalline solid IZM-2 advantageously consists in preparing an aqueous reaction mixture, called a gel, containing at least one source of at least one oxide $XO_2$, optionally at least one source of at least one oxide $Y_2O_3$, at least one organic species R, optionally at least one source of at least one alkali metal and/or alkaline-earth metal of the valency n. The amounts of said reagents are advantageously adjusted so as to give this gel a composition enabling its crystallization as a crystalline solid IZM-2 in its crude synthetic form of general formula (I) $XO_2:aY_2O_3:bM_{2/n}O:cR:dH_2O$, in which a, b, c and d meet the criteria defined above when c and d are greater than 0. The gel is then subjected to a hydrothermal treatment until said crystalline solid IZM-2 forms. The gel is advantageously placed under hydrothermal conditions at an autogenous reaction pressure, optionally with addition of gas, for example nitrogen, at a temperature of between 120° C. and 200° C., preferably between 140° C. and 180° C. and even more preferably between 160 and 175° C., until crystals of solid IZM-2 in its crude synthetic form have formed. The time required to obtain crystallization generally ranges between 1 hour and several months as a function of the composition of the reagents in the gel, the stirring and the reaction temperature. Preferably, the crystallization time ranges between 2 hours and 21 days. The reaction is generally performed with or without stirring, preferably with stirring.

It may be advantageous to add seeds to the reaction mixture in order to reduce the time required for formation of the crystals and/or the total crystallization time. It may also be advantageous to use seeds in order to promote the formation of said crystalline solid IZM-2 at the expense of impurities. Such seeds advantageously comprise crystalline solids, notably solid IZM-2 crystals. The crystalline seeds are generally added in a proportion of between 0.01% and 10% of the mass of the oxide $XO_2$ used in the reaction mixture.

On conclusion of the hydrothermal treatment step leading to crystallization of said solid IZM-2, the solid phase is advantageously filtered off, washed, dried and then calcined. The calcination step is advantageously performed via one or more heating steps performed at a temperature of between 100 and 1000° C., preferably between 400 and 650° C., for a time of between a few hours and several days, preferably between 3 hours and 48 hours. Preferably, the calcination is performed in two consecutive heating steps.

On conclusion of said calcination step, said solid IZM-2 obtained is advantageously the one having the X-ray diffraction diagram including at least the lines recorded in Table 1. It is free of water and also of the organic species R present in the solid IZM-2 in its crude synthetic form. After said calcination step, the IZM-2 zeolite may typically contain from 2000 to 8000 ppm of alkali metal and/or alkaline-earth metal element and preferably of sodium.

After calcination, so as to reduce the content of alkali metal and/or alkaline-earth metal and preferably of sodium, in said zeolite, the solid IZM-2 included in the composition of the support for the catalyst according to the invention is advantageously washed by means of at least one treatment with a solution of at least one ammonium salt so as to obtain the ammonium form of the solid IZM-2. The M/Y atomic ratio is generally advantageously less than 0.1, preferably less than 0.05 and even more preferably less than 0.01. This washing step may be performed at any step in the preparation of the support for the catalyst or of the catalyst, i.e. after the step of preparing the solid IZM-2, after the step of forming the solid IZM-2, or after the step of introducing the hydro-dehydrogenating metal. Preferably, the washing step is performed after the step of forming the solid IZM-2. The washing step is preferably performed by immersion with stirring of the solid in an aqueous solution of at least one ammonium salt. The ammonium salt may be chosen from ammonium nitrate NH4NO3, ammonium chloride NH4Cl, ammonium hydroxide NH4OH, ammonium bicarbonate NH4HCO3, ammonium acetate NH4H3C2O2 or ammonium sulfate (NH4)2SO4. The duration of immersion of the solid in the solution may typically range from 15 minutes to several hours. The concentration of ammonium salt(s) in the solution is typically between 0.1 mol per litre and 10 mol per litre. The washing is preferably performed at a temperature between room temperature and 100° C. The ratio between the volume of solution engaged (in ml) and the mass of zeolite engaged (in g) is preferably between 1 and 100. To reduce the content of alkali metal and/or alkaline-earth metal and preferably of sodium to the desired level, it may prove necessary to repeat the washing step several times. On conclusion of the final wash, the solid is filtered off, washed with deionized water and then dried. The IZM-2 zeolite is finally calcined so as to obtain it in its protonic form. The calcination conditions are typically the same as those used for calcining the solid on conclusion of the hydrothermal treatment step.

After washing, the zeolite may typically contain less than 200 ppm and preferably more than 20 ppm or even more than 30 ppm of alkali metal and/or alkaline-earth metal element and preferably of sodium.

Matrix

In accordance with the invention, the catalyst comprises at least one matrix. Said matrix may advantageously be amorphous or crystalline.

Preferably, said matrix is advantageously chosen from the group formed by alumina, silica, silica-alumina, clays, titanium oxide, boron oxide and zirconia, taken alone or as a mixture, or else aluminates may also be chosen. Preferably, alumina is used as matrix. Preferably, said matrix contains alumina in all its forms known to those skilled in the art, for instance aluminas of alpha, gamma, eta and delta type. Said aluminas differ in their specific surface area and their pore volume. The alkali metal and/or alkaline-earth metal content of the matrix is variable and depends on the method for obtaining said matrix, as is well known for alumina, for example (Handbook of Porous Solids, 2008, Wiley-VCH chapter 4.7.2).

The support for the catalyst used in the invention comprises and preferably consists of said matrix and of said IZM-2 zeolite.

The alkali metal and/or alkaline-earth metal content of the matrix may advantageously be adjusted via any method known to those skilled in the art for obtaining a catalyst in accordance with the invention. The matrix or the matrix precursor may thus be washed by placing it in contact with an aqueous solution whose pH is less than or equal to the point of zero charge of said matrix, as is illustrated for an alumina matrix in Catalysis Supports and Supported Catalysts, Butterworth Publishers (1987). By way of illustration, boehmite may be washed by placing said solid in contact with aqueous ammonium nitrate solution. The duration of immersion of the solid in the solution may typically range from 15 minutes to several hours. The concentration of ammonium salt(s) in the solution is typically between 0.1 mol per litre and 10 mol per litre. The washing is preferably performed at a temperature between room temperature and 100° C. The ratio between the volume of solution engaged (in ml) and the mass of boehmite engaged (in g) is preferably between 1 and 100. To reduce the content of alkali metal and/or alkaline-earth metal to the desired level, it may prove necessary to repeat the washing step several times. On conclusion of the final wash, the solid is filtered off, washed with deionized water and then dried and calcined.

When it contains alkali metal and/or alkaline-earth metal elements, the matrix may typically contain less than 200 ppm and preferably more than 20 ppm or even more than 30 ppm of alkali metal and/or alkaline-earth metal element and preferably of sodium.

Metal Phase

In accordance with the invention, the catalyst comprises at least one group VIII metal preferably chosen from iron, cobalt, nickel, ruthenium, rhodium, palladium, osmium, iridium and platinum, preferably chosen from the noble metals of group VIII, very preferably chosen from palladium and platinum and even more preferably platinum is chosen.

Preferably, said catalyst comprises a content of group VIII metal of between 0.01% and 5% by weight relative to the total mass of said catalyst and preferably between 0.1% and 4% by weight.

In the case where said catalyst comprises at least one noble metal from group VIII, the content of noble metal of said catalyst is advantageously between 0.01% and 5% by weight, preferably between 0.1% and 4% by weight and very preferably between 0.1% and 2% by weight relative to the total mass of said catalyst.

The catalyst of the invention may also advantageously contain at least one metal chosen from the metals of groups IIIA, IVA and VIIB chosen from gallium, indium, tin and rhenium. In this case, the content of metal chosen from the metals of groups IIIA, IVA and VIIB is preferably between 0.01% and 2%, preferably between 0.05% and 1% by weight relative to the total weight of said catalyst.

The dispersion of the group VIII metal(s), determined by chemisorption, for example by H2/O2 titration or by carbon monoxide chemisorption, is between 10% and 100%, preferably between 20% and 100% and more preferably between 30% and 100%. The macroscopic distribution coefficient for the metal(s) of group VIII, obtained from its (their) profile determined with a Castaing microprobe, defined as the ratio of the concentrations of the metal(s) of group VIII at the core of the grain relative to at the edge of this same grain, is between 0.7 and 1.3 and preferably between 0.8 and 1.2. The value of this ratio, in the region of 1, is evidence of the homogeneity of distribution of the metal(s) of group VIII in the catalyst.

Preparation of the Catalyst

The catalyst according to the invention may advantageously be prepared according to any of the methods well known to those skilled in the art.

Forming

Advantageously, the various constituents of the support of the catalyst can be formed by means of a blending step so as to form a paste, then extrusion of the paste obtained, or else by mixing powders then pelletizing, or else by any other known process for agglomeration of a powder containing alumina. The supports thus obtained may be in various shapes and sizes. Preferably, the forming is carried out by blending and extrusion.

During the forming of the support by blending and then extrusion, said IZM-2 zeolite may be introduced during the dissolution or suspension of the alumina compounds or alumina precursors, for instance boehmite. Said IZM-2 zeolite may be, for example, without this being limiting, in the form of a powder, a ground powder, a suspension, or a suspension which has undergone a deagglomeration treatment. Thus, for example, said zeolite may advantageously be placed in acidified or non-acidified suspension at a concentration adjusted to the final IZM-2 content targeted in the catalyst according to the invention. This suspension commonly referred to as a slip is then mixed with the alumina compounds or alumina precursors.

Moreover, the use of additives may advantageously be performed to facilitate the forming and/or to improve the final mechanical properties of the supports, as is well known to those skilled in the art. Examples of additives that may notably be mentioned include cellulose, carboxymethylcellulose, carboxyethylcellulose, tall oil, xanthan gums, surfactants, flocculants such as polyacrylamides, carbon black, starches, stearic acid, polyacryl alcohol, polyvinyl alcohol, biopolymers, glucose, polyethylene glycols, etc.

Water may advantageously be added or removed to adjust the viscosity of the paste to be extruded. This step may advantageously be performed at any stage in the blending step.

To adjust the solids content of the paste to be extruded so as to make it extrudable, a compound that is predominantly solid, preferably an oxide or a hydrate, may also be added. A hydrate is preferably used, and even more preferably an aluminium hydrate. The loss on ignition of this hydrate is advantageously greater than 15%.

Extrusion of the paste derived from the blending step may advantageously be performed with any conventional commercially available tool. The paste derived from the blending is advantageously extruded through a die, for example using a piston or a single-screw or twin-screw extruder. The extrusion may advantageously be performed via any method known to those skilled in the art.

The catalyst supports according to the invention are generally in the form of cylindrical extrudates or polylobal extrudates such as bilobal, trilobal or polylobal extrudates of straight or twisted form, but may optionally be manufactured and used in the form of crushed powders, lozenges, rings, beads and/or wheels. Preferably, the catalyst supports according to the invention are in the form of spheres or extrudates. Advantageously, the support is in the form of extrudates with a diameter of between 0.5 and 5 mm and more particularly between 0.7 and 2.5 mm. The forms may be cylindrical (which may or may not be hollow) and/or twisted and/or multilobal (for example 2, 3, 4 or 5 lobes) cylindrical and/or annular. The multilobal form is advantageously preferably used.

Drying

The support thus obtained may then be subjected to a drying step. Said drying step is advantageously performed via any technique known to those skilled in the art.

Preferably, the drying is performed under a stream of air. Said drying may also be performed under a stream of any oxidizing, reducing or inert gas. Preferably, the drying is advantageously performed at a temperature of between 50 and 180° C., preferably between 60 and 150° C. and very preferably between 80 and 130° C.

Calcination

Said support, optionally dried, then preferably undergoes a calcination step.

Said calcination step is advantageously performed in the presence of molecular oxygen, for example by flushing with air, at a temperature advantageously greater than 200° C. and less than or equal to 1100° C. Said calcination step may advantageously be performed in a traversed bed, in a licked bed or under a static atmosphere. For example, the oven used may be a rotary oven or may be a vertical oven with radial traversed layers. Preferably, said calcination step is performed for between more than one hour at 200° C. and less than one hour at 1100° C. The calcination may advantageously be performed in the presence of steam and/or in the presence of an acidic or basic vapour. For example, the calcination may be performed under a partial pressure of ammonia.

Post-Calcination Treatments

Post-calcination treatments may optionally be performed, so as to improve the properties of the support, notably the textural properties.

Thus, the catalyst support according to the present invention may be subjected to a hydrothermal treatment in a confined atmosphere. The term "hydrothermal treatment in a confined atmosphere" means a treatment in an autoclave in the presence of water at a temperature above room temperature, preferably above 25° C., preferably above 30° C.

In the course of this hydrothermal treatment, the support may advantageously be impregnated, prior to its treatment in the autoclave (the autoclaving being done either in the vapour phase or in the liquid phase, this vapour or liquid phase of the autoclave possibly being acidic or not). This impregnation, prior to autoclaving, may advantageously be acidic or not. This impregnation, prior to autoclaving, may advantageously be performed dry or by immersing the support in an acidic aqueous solution. The term "dry impregnation" means placing the support in contact with a volume of solution less than or equal to the total pore volume of the support. Preferably, the impregnation is performed dry. The autoclave is preferably a rotating-basket autoclave such as the one defined in patent application EP 0 387 109 A. The temperature during the autoclaving may be between 100 and 250° C. for a period of time of between 30 minutes and 3 hours.

The formed mixture of the matrix and of IZM-2 zeolite constitutes the support for the catalyst. The alkali metal and/or alkaline-earth metal content of the support may also be adjusted via any method known to those skilled in the art for obtaining a catalyst in accordance with the invention.

Preferably, washing treatments may also be performed in order to reduce the alkali metal and/or alkaline-earth metal content of the support. The operating conditions of the washing are typically the same as those described for the washing of the zeolite. The support is then calcined again after washing, preferably under the same conditions as those described for the washing of the zeolite.

Deposition of the Metal Phase

For the deposition of the metal from group VIII of the Periodic Table of the Elements, any deposition technique known to those skilled in the art and any precursor of such metals may be suitable for use. Use may be made of the deposition techniques by dry impregnation or excess impregnation of a solution containing the precursors of the metals, in the presence or absence of competitors. The introduction of the metal may be performed in any step of the preparation of the catalyst: on the IZM-2 zeolite and/or on the matrix, notably before the forming step, during the forming step, or after the forming step, on the support for the catalyst. Preferably, the deposition of the metal is performed after the forming step.

The control of certain parameters used during the deposition, in particular the nature of the precursor of the group VIII metal(s) used, makes it possible to direct the deposition of said metal(s) predominantly on the matrix or on the zeolite.

Thus, to introduce the group VIII metal(s), preferentially platinum and/or palladium, predominantly on the matrix, an anionic exchange may be performed with hexachloroplatinic acid and/or hexachlorpalladic acid, in the presence of a competing agent, for example hydrochloric acid, the deposition generally being followed by calcination, for example at a temperature of between 350 and 550° C., and for a period of between 1 and 4 hours. With such precursors, the group VIII metal(s) is (are) deposited predominantly on the matrix and said metal(s) show(s) good dispersion and good macroscopic distribution through the catalyst grain.

It is also possible to envisage depositing the group VIII metal(s), preferentially platinum and/or palladium, by cationic exchange such that said metal(s) are predominantly on the zeolite. Thus, in the case of platinum, the precursor may be chosen, for example, from:

ammoniacal compounds such as platinum(II) tetramine salts of formula Pt(NH3)4X2; platinum(IV) hexamine salts of formula Pt(NH3)6X4; platinum(IV) halopentamine salts of formula (PtX(NH3)5)X3; platinum N-tetrahalodiamine salts of formula PtX4(NH3)2; and halogenated compounds of formula H(Pt(acac)2X);

X being a halogen chosen from the group formed by chlorine, fluorine, bromine and iodine, X preferably being chlorine, and "acac" representing the acetylacetonate group (of empirical formula C5H7O2), derived from acetylacetone. With such precursors, the group VIII metal(s) is (are) deposited predominantly on the zeolite and said metal(s) show(s) good dispersion and good macroscopic distribution through the catalyst grain.

The impregnation solution may also advantageously comprise at least one ammonium salt chosen from ammonium nitrate NH4NO3, ammonium chloride NH4Cl, ammonium hydroxide NH4OH, ammonium bicarbonate NH4HCO3 and ammonium acetate NH4H3C2O2, alone or as a mixture, the mole ratio between the ammonium salt and the noble metal of the precursor being between 0.1 and 400.

In the case where the catalyst of the invention also contains at least one metal chosen from the metals from groups IIIA, IVA and VIIB, any technique for deposition of such a metal that are known to those skilled in the art and any precursor of such metals may be suitable for use.

The group VIII metal(s) and that (those) of groups IIIA, IVA and VIIB may be added either separately or simultaneously in at least one unit step. When at least one metal from groups IIIA, IVA and VIIB is added separately, it is preferable for it to be added after the group VIII metal.

The additional metal chosen from the metals from groups IIIA, IVA and VIIB may be introduced by means of compounds such as, for example, chlorides, bromides and nitrates of the metals from groups IIIA, IVA and VIIB. For example, in the case of indium, the nitrate or the chloride is advantageously used, and, in the case of rhenium, perrhenic acid is advantageously used. The additional metal chosen from the metals from groups IIIA, IVA and VIIB may also be introduced in the form of at least one organic compound chosen from the group consisting of complexes of said metal, in particular polyketone complexes of the metal and hydrocarbylmetals such as alkyl, cycloalkyl, aryl, alkylaryl and arylalkyl metals. In the latter case, the introduction of the metal is advantageously performed using a solution of the organometallic compound of said metal in an organic solvent. Organohalogen compounds of the metal may also be used. Organic compounds of metals that may be mentioned in particular include tetrabutyltin, in the case of tin, and triphenylindium, in the case of indium.

If the additional metal chosen from the metals from groups IIIA, IVA and VIIB is introduced before the metal from group VIII, the compound of the IIIA, IVA and/or VIIB metal used is generally chosen from the group constituted by the halide, nitrate, acetate, tartrate, carbonate and oxalate of the metal. The introduction is then advantageously performed in an aqueous solution. However, it may also be introduced using a solution of an organometallic compound of the metal, for example tetrabutyltin. In this case, before introducing at least one group VIII metal, calcination in air will be performed.

Furthermore, intermediate treatments, for instance calcination and/or reduction, may be applied between the successive depositions of the various metals.

After calcination, washing treatments may also be performed in order to adjust the alkali metal and alkaline-earth metal content of the catalyst. The operating conditions of the washing are typically the same as those described for the washing of the zeolite. The catalyst is then calcined once again after washing.

Before its use in an isomerization process, the catalyst according to the invention is preferably reduced. This reduction step is advantageously performed by treatment under hydrogen at a temperature of between 150° C. and 650° C. at a total pressure of between 0.1 and 25 MPa. For example, a reduction consists of a stage at 150° C. for two hours and then a temperature increase to 450° C. at a rate of 1° C./minute, and then a stage of two hours at 450° C.; throughout this reduction step, the hydrogen flow rate is 1000 normal m3 of hydrogen per tonne of catalyst and the total pressure is kept constant at 0.2 MPa. Any ex-situ reduction method may advantageously be envisaged. Prior reduction of the final catalyst ex-situ, under a stream of hydrogen, may be performed, for example at a temperature of from 450° C. to 600° C., for a time of from 0.5 to 4 hours.

Said catalyst also advantageously comprises sulfur. In the case where the catalyst of the invention contains sulfur, said sulfur may be introduced at any step in the preparation of the catalyst: before or after the forming and/or drying and/or calcination step, before or after the introduction of the metal(s) mentioned previously, or alternatively by in-situ and/or ex-situ sulfurization before the catalytic reaction. In the case of in-situ sulfurization, the reduction, if the catalyst has not been reduced beforehand, takes place before the sulfurization. In the case of ex-situ sulfurization, the reduction is also performed, followed by sulfurization. The sulfurization is preferably performed in the presence of hydrogen using any sulfurizing agent that is well known to those skilled in the art, for instance dimethyl sulfide or hydrogen sulfide.

The catalysts according to the invention are in various shapes and sizes. They are generally used in the form of cylindrical extrudates and/or polylobal extrudates such as bilobal, trilobal or polylobal extrudates of straight and/or twisted form, but may optionally be manufactured and used in the form of crushed powders, lozenges, rings, beads and/or wheels. Preferably, the catalysts used in the process according to the invention are in the form of spheres or extrudates. Advantageously, the catalyst is in the form of extrudates with a diameter of between 0.5 and 5 mm and more particularly between 0.7 and 2.5 mm. The forms may be cylindrical (which may or may not be hollow) and/or twisted and/or multilobal (for example 2, 3, 4 or 5 lobes) cylindrical and/or annular. The multilobal form is advantageously preferably used. The metal deposit does not change the form of the support.

The Isomerization Process

A subject of the present invention is also a process for the isomerization of a cut containing at least one aromatic compound containing eight carbon atoms per molecule, said process comprising placing said aromatic cut in contact with at least said catalyst according to the invention present in a catalytic reactor.

Said aromatic cut containing at least one aromatic compound containing eight carbon atoms per molecule in particular comprises as aromatic compound containing eight carbon atoms per molecule either solely a mixture of xylenes, or solely ethylbenzene, or a mixture of xylene(s) and of ethylbenzene.

Said isomerization process is generally performed according to the following operating conditions:
- a temperature of from 300° C. to 500° C., preferably from 320° C. to 450° C. and even more preferably from 340° C. to 430° C.;
- a partial pressure of hydrogen of between 0.3 and 1.5 MPa, preferably between 0.4 and 1.2 MPa and more preferably from 0.7 to 1.2 MPa;
- a total pressure of from 0.45 to 1.9 MPa, preferably from 0.6 to 1.5 MPa; and
- a feed space velocity, expressed in kilograms of feedstock introduced per kilogram of catalyst and per hour, of from 0.25 to 30 h-1, preferably from 1 to 10 h-1 and even more preferably from 2 to 6 h-1.

The examples that follow illustrate the invention without, however, limiting its scope.

EXAMPLES

Example 1: Synthesis of IZM-2 Zeolite

IZM-2 zeolite was synthesized in accordance with the teaching of patent FR 2 918 050 B. A colloidal silica suspension known under the trade name Ludox HS-40, sold by Aldrich, is incorporated into a solution composed of sodium hydroxide (Prolabo), 1,6-bis(methylpiperidinium) hexane dibromide structuring agent, aluminium hydroxide (Aldrich) and deionized water. The molar composition of the mixture is as follows: 1 SiO2; 0.0042 Al2O3; 0.1666 Na2O; 0.1666 1,6-bis(methylpiperidinium)hexane; 33.3333 H2O. The mixture is stirred vigorously for 30 minutes. The mixture is then transferred, after homogenization, into a Parr autoclave. The autoclave is heated for 5 days at 170° C. with spindle stirring (30 rpm). The product obtained is filtered, washed with deionized water to reach neutral pH and then dried overnight at 100° C. in an oven. The solid is then introduced into a muffle furnace and calcined so as to remove the structuring agent. The calcination cycle comprises a temperature rise up to 200° C., a stage of two hours at this temperature, a temperature rise up to 550° C., followed by a stage of eight hours at this temperature and finally a return to room temperature. The temperature rises are performed with a gradient of 2° C./minute. The solid thus obtained has a sodium content, measured by atomic absorption, of 3695 ppm.

To reduce the sodium content, the solid thus obtained is then refluxed for 2 hours in an aqueous ammonium nitrate solution (10 ml of solution per gram of solid, ammonium nitrate concentration of 3M). This refluxing step is performed four times with fresh ammonium nitrate solution, and the solid is then filtered off, washed with deionized water and dried in an oven overnight at 100° C. Finally, to obtain the zeolite in its acid (protonated H+) form, a step of calcination is performed at 550° C. for 10 hours (temperature increase rate of 2° C./minute) in a traversed bed under dry air (2 normal litres per hour and per gram of solid). The solid thus obtained was analysed by X-ray diffraction and identified as being constituted by IZM-2 zeolite. The solid thus obtained has a sodium content, measured by atomic absorption, of 142 ppm.

Example 2: Preparation of a First IZM-2/Alumina Support

The IZM-2/alumina support is obtained by blending and extrusion of the IZM-2 zeolite prepared in Example 1 with a first batch of boehmite supplied by the company Axens, containing 268 ppm by weight of sodium. The blended paste is extruded through a quadrilobal die 1.5 mm in diameter. After drying in an oven overnight at 110° C., the extrudates are calcined at 550° C. for two hours (temperature increase rate of 5° C./minute) in a crossed bed under dry air (2 normal litres per hour and per gram of solid). The support does not undergo a washing step. The weight content of IZM-2 zeolite in the support after calcination is 14% by weight. The sodium content in the support, measured by atomic absorption, is 250 ppm.

Example 3 (not in Accordance with the Invention): Preparation of an Isomerization Catalyst A Catalyst A is a catalyst comprising an IZM-2 zeolite, platinum and an alumina matrix. This catalyst is prepared by dry impregnation of the IZM-2/alumina support prepared in Example 2 with an aqueous solution containing platinum tetramine nitrate Pt(NH3)4(NO3)2. 20 g of support are typically used, and are dry-impregnated in a rotating barrel. After impregnation, the solid is left to mature for at least five hours in the laboratory air and is then dried overnight in an oven at 110° C. and, finally, a calcination step is performed under a flow of dry air (1 normal litre per hour and per gram of solid) in a tubular oven under the following conditions:
- temperature rise from room temperature to 150° C. at 5° C./min;
- stage of 1 hour at 150° C.;
- rise from 150° C. to 450° C. at 5° C./min;
- stage of 1 hour at 450° C.;
- decrease to room temperature.

The Pt content measured by XRF on the calcined catalyst is 0.3% by weight, and its coefficient of distribution measured by Castaing microprobe is 0.96. The catalyst obtained is not subjected to a step of washing with ammonium nitrate solution. The sodium content in the catalyst, measured by atomic absorption, is 245 ppm.

The textural properties of catalyst A were characterized by nitrogen porosimetry at 196° C. on a Micromeritics ASAP 2010 machine. Before nitrogen adsorption, the solid is degassed under vacuum at 90° C. for 1 hour and then at 350° C. for 4 hours. The total pore volume corresponds to the volume of nitrogen adsorbed at a relative pressure of 0.97. The specific surface area of the solid is calculated by means of the BET method and the median pore diameter calculated according to the BJH adsorption model corresponds to the diameter for which half of the volume of nitrogen is adsorbed. Catalyst A has a specific surface area of 294 $m^2/g$, a total pore volume of 0.74 ml/g and a median diameter of 12 nm.

Example 4: Preparation of a Second IZM-2/Alumina Support

The IZM-2/alumina support is obtained by blending and extrusion of the IZM-2 zeolite prepared in Example 1 with a second batch of boehmite supplied by the company Axens. This second batch of boehmite differs from the first batch by its lower sodium content, the second batch of boehmite containing 63 ppm by weight of sodium. The blended paste is extruded through a quadrilobal die 1.5 mm in diameter. After drying in an oven overnight at 110° C., the extrudates are calcined at 550° C. for two hours (temperature increase rate of 5° C./minute) in a traversed bed under dry air (2 normal litres per hour and per gram of solid). The second support does not undergo a washing step. The weight content of IZM-2 zeolite in the support after calcination is 14% by weight. The sodium content in the support, measured by atomic absorption, is 74 ppm.

Example 5 (in Accordance with the Invention): Preparation of an Isomerization Catalyst B Catalyst B is a catalyst comprising an IZM-2 zeolite, platinum and an alumina matrix. This catalyst is prepared by dry impregnation of the IZM-2/alumina support prepared in Example 3 with an aqueous solution containing platinum tetramine nitrate Pt(NH3)4(NO3)2. 20 g of support are typically used, and are dry-impregnated in a rotating barrel. After impregnation, the solid is left to mature for at least five hours in the laboratory air and is then dried overnight in an oven at 110° C. and, finally, a calcination step is performed under a flow of dry air (1 normal litre per hour and per gram of solid) in a tubular oven under the following conditions:
  temperature rise from room temperature to 150° C. at 5° C./min;
  stage of 1 hour at 150° C.;
  rise from 150° C. to 450° C. at 5° C./min;
  stage of 1 hour at 450° C.;
  decrease to room temperature.

The Pt content measured by XRF on the calcined catalyst is 0.3% by weight, and its coefficient of distribution measured by Castaing microprobe is 1.03. The catalyst obtained is not subjected to a step of washing with ammonium nitrate solution. The sodium content in the catalyst, measured by atomic absorption, is 69 ppm.

The textural properties of catalyst B were characterized by nitrogen porosimetry at 196° C. on a Micromeritics ASAP 2010 machine. Before nitrogen adsorption, the solid is degassed under vacuum at 90° C. for 1 hour and then at 350° C. for 4 hours. The total pore volume corresponds to the volume of nitrogen adsorbed at a relative pressure of 0.97. The specific surface area of the solid is calculated by means of the BET method and the median pore diameter calculated according to the BJH adsorption model corresponds to the diameter for which half of the volume of nitrogen is adsorbed. Catalyst B has a specific surface area of 298 $m^2/g$, a total pore volume of 0.76 ml/g and a median diameter of 13 nm.

Example 6: Preparation of a Third IZM-2/Alumina Support

The IZM-2/alumina support is obtained by blending and extrusion of the IZM-2 zeolite prepared in Example 1 with a third batch of boehmite supplied by the company Axens, containing 130 ppm by weight of sodium. The blended paste is extruded through a quadrilobal die 1.5 mm in diameter. After drying in an oven overnight at 110° C., the extrudates are calcined under the following conditions:
  temperature rise from room temperature to 150° C. at 5° C./min in dry air (1 normal litre per hour and per gram of solid),
  stage of 1 hour at 150° C. in dry air (1 normal litre per hour and per gram of solid),
  rise from 150 to 550° C. at 5° C./min in dry air (1 normal litre per hour and per gram of solid) up to 480° C., and then in a mixture of air and water (30% by volume of water) starting from 480° C.,
  stage of 2 hours at 550° C. in a mixture of air and water (1 normal litre per hour and per gram of solid),
  decrease to 480° C. in a mixture of air and water (1 normal litre per hour and per gram of solid),
  decrease from 480° C. to room temperature in dry air (1 normal litre per hour and per gram of solid).

The support does not undergo a washing step. The weight content of IZM-2 zeolite in the support after calcination is 13% by weight. The sodium content in the support, measured by atomic absorption, is 132 ppm.

Example 7 (in Accordance with the Invention): Preparation of an Isomerization Catalyst C Catalyst C is a catalyst comprising a zeolite IZM-2, platinum and an alumina matrix. This catalyst is prepared by dry impregnation of the IZM-2/alumina support prepared in Example 6 with an aqueous solution containing platinum tetramine nitrate Pt(NH3)4(NO3)2. 20 g of support are typically used, and are dry-impregnated in a rotating barrel. After impregnation, the solid is left to mature for at least five hours in the laboratory air and is then dried overnight in an oven at 110° C. and, finally, a calcination step is performed under a flow of dry air (1 normal litre per hour and per gram of solid) in a tubular oven under the following conditions:
  temperature rise from room temperature to 150° C. at 5° C./min,
  stage of 1 hour at 150° C.,
  rise from 150° C. to 450° C. at 5° C./min,
  stage of 1 hour at 450° C.,
  decrease to room temperature.

The Pt content measured by XRF on the calcined catalyst is 0.26% by weight, and its coefficient of distribution measured by Castaing microprobe is 1.1. The catalyst obtained is not subjected to a step of washing with ammonium nitrate solution. The sodium content in the catalyst, measured by atomic absorption, is 130 ppm.

The textural properties of catalyst C were characterized by nitrogen porosimetry at 196° C. on a Micromeritics ASAP 2010 machine. Before nitrogen adsorption, the solid is degassed under vacuum at 90° C. for 1 hour and then at 350° C. for 4 hours. The total pore volume corresponds to the volume of nitrogen adsorbed at a relative pressure of 0.97. The specific surface area of the solid is calculated by means of the BET method and the median pore diameter calculated according to the BJH adsorption model corresponds to the diameter for which half of the volume of nitrogen is adsorbed. Catalyst C has a specific surface area of 268 m$^2$/g, a total pore volume of 0.73 ml/g and a median diameter of 14.5 nm.

Example 8: Preparation of a Fourth IZM-2/Alumina Support

The IZM-2/alumina support is obtained by blending and extrusion of the IZM-2 zeolite prepared in Example 1 with a fourth batch of boehmite supplied by the company Axens, containing 297 ppm by weight of sodium. The blended paste is extruded through a quadrilobal die 1.5 mm in diameter. After drying in an oven overnight at 110° C., the extrudates are calcined under the following conditions:
  temperature rise from room temperature to 150° C. at 5° C./min in dry air (1 normal litre per hour and per gram of solid),
  stage of 1 hour at 150° C. in dry air (1 normal litre per hour and per gram of solid),
  rise from 150 to 550° C. at 5° C./min in dry air (1 normal litre per hour and per gram of solid) up to 480° C., and then in a mixture of air and water (30% by volume of water) starting from 480° C.,
  stage of 2 hours at 550° C. in a mixture of air and water (1 normal litre per hour and per gram of solid),
  decrease to 480° C. in a mixture of air and water (1 normal litre per hour and per gram of solid),
  decrease from 480° C. to room temperature in dry air (1 normal litre per hour and per gram of solid).

The support does not undergo a washing step. The weight content of IZM-2 zeolite in the support after calcination is 13% by weight. The sodium content in the support, measured by atomic absorption, is 276 ppm.

Example 9 (not in Accordance with the Invention): Preparation of an Isomerization Catalyst D Catalyst D is a catalyst comprising a zeolite IZM-2, platinum and an alumina matrix. This catalyst is prepared by dry impregnation of the IZM-2/alumina support prepared in Example 8 with an aqueous solution containing platinum tetramine nitrate Pt(NH3)4(NO3)2. 20 g of support are typically used, and are dry-impregnated in a rotating barrel. After impregnation, the solid is left to mature for at least five hours in the laboratory air and is then dried overnight in an oven at 110° C. and, finally, a calcination step is performed under a flow of dry air (1 normal litre per hour and per gram of solid) in a tubular oven under the following conditions:
  temperature rise from room temperature to 150° C. at 5° C./min,
  stage of 1 hour at 150° C.,
  rise from 150° C. to 450° C. at 5° C./min,
  stage of 1 hour at 450° C.,
  decrease to room temperature.

The Pt content measured by XRF on the calcined catalyst is 0.26% by weight, and its coefficient of distribution measured by Castaing microprobe is 1.0. The catalyst obtained is not subjected to a step of washing with ammonium nitrate solution. The sodium content in the catalyst, measured by atomic absorption, is 278 ppm.

The textural properties of catalyst D were characterized by nitrogen porosimetry at 196° C. on a Micromeritics ASAP 2010 machine. Before nitrogen adsorption, the solid is degassed under vacuum at 90° C. for 1 hour and then at 350° C. for 4 hours. The total pore volume corresponds to the volume of nitrogen adsorbed at a relative pressure of 0.97. The specific surface area of the solid is calculated by means of the BET method and the median pore diameter calculated according to the BJH adsorption model corresponds to the diameter for which half of the volume of nitrogen is adsorbed. Catalyst D has a specific surface area of 276 m$^2$/g, a total pore volume of 0.69 ml/g and a median diameter of 13 nm.

Example 10: Preparation of a Fourth IZM-2/Alumina Support

The IZM-2/alumina support is obtained by blending and extrusion of the IZM-2 zeolite prepared in Example 1 with a fourth batch of boehmite supplied by the company Axens, containing 84 ppm by weight of sodium. The blended paste is extruded through a quadrilobal die 1.5 mm in diameter. After drying in an oven overnight at 110° C., the extrudates are calcined under the following conditions:
  temperature rise from room temperature to 150° C. at 5° C./min in dry air (1 normal litre per hour and per gram of solid),
  stage of 1 hour at 150° C. in dry air (1 normal litre per hour and per gram of solid),
  rise from 150 to 550° C. at 5° C./min in dry air (1 normal litre per hour and per gram of solid) up to 480° C., and then in a mixture of air and water (30% by volume of water) starting from 480° C.,
  stage of 2 hours at 550° C. in a mixture of air and water (1 normal litre per hour and per gram of solid),
  decrease to 480° C. in a mixture of air and water (1 normal litre per hour and per gram of solid),
  decrease from 480° C. to room temperature in dry air (1 normal litre per hour and per gram of solid).

The support does not undergo a washing step. The weight content of IZM-2 zeolite in the support after calcination is 13% by weight. The sodium content in the support, measured by atomic absorption, is 91 ppm.

Example 11 (in Accordance with the Invention): Preparation of an Isomerization Catalyst E Catalyst E is a catalyst comprising a zeolite IZM-2, platinum and an alumina matrix. This catalyst is prepared by dry impregnation of the IZM-2/alumina support prepared in Example 10 with an aqueous solution containing platinum tetramine nitrate Pt(NH3)4(NO3)2. 20 g of support are typically used, and are dry-impregnated in a rotating barrel. After impregnation, the solid is left to mature for at least five hours in the laboratory air and is then dried overnight in an oven at 110° C. and, finally, a calcination step is performed under a flow of dry air (1 normal litre per hour and per gram of solid) in a tubular oven under the following conditions:
  temperature rise from room temperature to 150° C. at 5° C./min,
  stage of 1 hour at 150° C.,
  rise from 150° C. to 450° C. at 5° C./min,
  stage of 1 hour at 450° C.,
  decrease to room temperature.

The Pt content measured by XRF on the calcined catalyst is 0.27% by weight, and its coefficient of distribution measured by Castaing microprobe is 0.96. The catalyst obtained is not subjected to a step of washing with ammonium nitrate solution. The sodium content in the catalyst, measured by atomic absorption, is 89 ppm.

The textural properties of catalyst E were characterized by nitrogen porosimetry at 196° C. on a Micromeritics ASAP 2010 machine. Before nitrogen adsorption, the solid is degassed under vacuum at 90° C. for 1 hour and then at 350° C. for 4 hours. The total pore volume corresponds to the volume of nitrogen adsorbed at a relative pressure of 0.97. The specific surface area of the solid is calculated by means of the BET method and the median pore diameter calculated according to the BJH adsorption model corresponds to the diameter for which half of the volume of nitrogen is adsorbed. Catalyst D has a specific surface area of 272 m²/g, a total pore volume of 0.67 ml/g and a median diameter of 12 nm.

Example 12: Evaluation of the Catalytic Properties of Catalysts a, B, C, D and E in the Isomerization of an Aromatic C8 Cut The catalysts were tested in the isomerization of an aromatic C8 cut composed of ethylbenzene (19% by weight), ortho-xylene (16% by weight), meta-xylene (58% by weight) and ethylcyclohexane (7% by weight). The tests were performed in a micro-unit using a fixed-bed reactor and working in a descending stream without recycling. The analysis of the hydrocarbon-based effluents is performed online by gas chromatography. Before loading into the unit, the catalyst is first dried at least overnight in an oven at 110° C. Once loaded into the unit, the catalyst undergoes a first drying step under nitrogen under the following conditions:
nitrogen flow rate: 5 normal litres per hour and per gram of catalyst,
total pressure: 1.3 MPa,
temperature increase rate from room temperature to 150° C.: 10° C./min,
stage at 150° C. for 30 minutes.

After drying, the nitrogen is replaced with hydrogen and a step of reduction under a flow of pure hydrogen is then performed under the following conditions:
hydrogen flow rate: 4 normal litres per hour and per gram of catalyst,
total pressure: 1.3 MPa,
temperature increase rate from 150 to 480° C.: 5° C./min,
stage at 480° C. for 2 hours.

The temperature is then reduced to 425° C. and the catalyst is then stabilized for 24 hours under a stream of hydrogen and of hydrocarbons (mixture of ethylbenzene at 20% by weight and ortho-xylene at 80% by weight), under the following operating conditions:
feed space velocity of 5 g of hydrocarbons per hour and per gram of catalyst,
mole ratio of hydrogen to hydrocarbons of 4,
total pressure of 1.3 MPa.

After the stabilization step, the temperature is reduced to 385° C. and the catalyst is placed in contact with the aromatic C8 cut mentioned above, under the following conditions:
feed space velocity of 3.5 g of the aromatic C8 cut per hour and per gram of catalyst,
mole ratio of hydrogen to hydrocarbons of 4,
total pressure of 0.86 MPa.

The catalyst is maintained for 7 hours under these operating conditions and the catalytic performance qualities are then evaluated according to the various operating conditions summarized in Table 2 below. Variation of the feed space velocity makes it possible to vary the levels of conversion into ethylbenzene and of xylene isomerization and thus the production of para-xylene. For each operating condition, two analyses by chromatography are performed in order to measure the performance qualities of the catalysts.

| conditions | 1 | 2 | 3 | 4 | 5 |
|---|---|---|---|---|---|
| Duration of each condition (h) | 2.8 | 2.1 | 2.1 | 2.1 | 2.1 |
| Temperature (° C.) | 385 | 385 | 385 | 385 | 385 |
| Feed space velocity ($h^{-1}$) | 3.5 | 4.5 | 6.0 | 9.0 | 12.0 |
| $H_2$/hydrocarbons (mol/mol) | 4 | 4 | 4 | 4 | 4 |
| Total pressure (MPa) | 0.86 | 0.86 | 0.86 | 0.86 | 0.86 |

The yield of para-xylene (PX) in the hydrocarbon effluent obtained at a feed space velocity of 12 h-1 makes it possible to evaluate the activity of the catalysts towards the production of para-xylene:
PX=weight % of para-xylene in the hydrocarbon effluent, where PX is the yield of para-xylene in weight %.

The change in the yield of net losses (NL) as a function of the yield of para-xylene makes it possible, for its part, to evaluate the selectivity of the catalyst. All the hydrocarbon molecules other than the cyclic molecules containing eight carbon atoms are considered as net losses.

$$NL=100-PX-EB-OX-MX-N8$$

with:
NL: yield of net losses in the hydrocarbon effluent, in weight %,
PX: weight % of para-xylene in the hydrocarbon effluent,
EB: weight % of ethylbenzene in the hydrocarbon effluent,
OX: weight % of ortho-xylene in the hydrocarbon effluent,
MX: weight % of meta-xylene in the hydrocarbon effluent,
N8: weight % of naphthenes containing eight carbon atoms in the hydrocarbon effluent.

Table 3 thus reports the para-xylene yield of catalysts A, B, C, D and E at a space velocity of 20 h-1 and also the net losses estimated for a para-xylene yield of 18% for the catalysts. The net losses (NL) at a para-xylene yield of 18% are estimated by linear interpolation or extrapolation of the experimental data for the change in the yield of net losses as a function of the para-xylene yield. It is observed that the five catalysts show identical net losses, and thus identical selectivities, for a para-xylene yield of 18%. On the other hand, they differ in their activity: catalysts B, C and E according to the invention with a reduced sodium content have higher activity than catalysts A and D not in accordance with the invention.

| Catalyst | A (comparative) | B | C | D (comparative) | E |
|---|---|---|---|---|---|
| Na content (ppm) | 245 | 71 | 130 | 278 | 89 |
| para-Xylene yield at a space velocity of 20 $h^{-1}$ | 14.1 | 16.4 | 16.7 | 16.1 | 16.9 |
| Yield of net losses at a para-xylene yield of 18% | 2.5 | 2.6 | 2.6 | 2.6 | 2.7 |

The invention claimed is:

1. A catalyst consisting of
   at least one IZM-2 zeolite containing silicon atoms and optionally aluminum atoms in an amount from 1 to 90% by weight, relative to a total mass of said catalyst;
   at least one matrix;
   at least one metal from group VIII of the Periodic Table of the Elements in an amount from about 0.01 to 5% by weight, relative to a total mass of said catalyst; and
   a total weight content of sodium in said catalyst is less than 200 ppm by weight and greater than 20 ppm by weight, relative to a total mass of the catalyst;
   wherein the at least one metal from group VIII of the Periodic Table of the Elements is platinum.

2. The catalyst according to claim 1, wherein the at least one matrix is selected from the group consisting of alumina, silica, silica-alumina, clays, titanium oxide, boron oxide, zirconia, and mixtures thereof.

3. The catalyst according to claim 1, wherein a total weight content of sodium in said catalyst is less than 150 ppm by weight and greater than 20 ppm by weight, relative to the total mass of said catalyst.

4. The catalyst according to claim 3, wherein a total weight content of sodium in said catalyst is less than 100 ppm by weight and greater than 20 ppm by weight, relative to the total mass of said catalyst.

5. The catalyst according to claim 4, wherein a total weight content of sodium in said catalyst is less than 90 ppm by weight and greater than 20 ppm by weight, relative to the total mass of said catalyst.

6. The catalyst according to claim 5, wherein a total weight content of sodium in said catalyst is less than 80 ppm by weight and greater than 20 ppm by weight, relative to the total mass of said catalyst.

7. The catalyst according to claim 6, wherein a total weight content of sodium in said catalyst is less than 70 ppm by weight and greater than 20 ppm by weight, relative to the total mass of said catalyst.

8. A process for the isomerization of an aromatic cut containing at least one aromatic compound containing eight carbon atoms per molecule, said process comprising placing said aromatic cut in contact with the catalyst according to claim 1 under the following operating conditions:
   a temperature of from 300° C. to 500° C.,
   a partial pressure of hydrogen of from 0.3 to 1.5 MPa,
   a total pressure of from 0.45 to 1.9 MPa, and
   a feed space velocity, expressed in kilograms of feedstock introduced per kilogram of catalyst and per hour, of from 0.25 to 30 h-1.

9. The isomerization process according to claim 8, in which said aromatic cut containing the at least one aromatic compound containing eight carbon atoms per molecule comprises as aromatic compound containing eight carbon atoms per molecule either solely a mixture of xylenes, or solely ethylbenzene, or a mixture of xylene(s) and of ethylbenzene.

* * * * *